(12) United States Patent
De Canniere

(10) Patent No.: US 7,022,126 B2
(45) Date of Patent: Apr. 4, 2006

(54) CLAMPING DEVICE FOR ANATOMICAL STRUCTURE

(75) Inventor: Bernard De Canniere, Brussels (BE)

(73) Assignee: Cardio Life Research S.A., Brussels (BE)

(*) Notice: Subject to any disclaimer, the term of this patent is extended or adjusted under 35 U.S.C. 154(b) by 0 days.

(21) Appl. No.: 10/343,312

(22) PCT Filed: Dec. 12, 2001

(86) PCT No.: PCT/BE01/00211

§ 371 (c)(1), (2), (4) Date: Apr. 15, 2003

(87) PCT Pub. No.: WO02/051321

PCT Pub. Date: Jul. 4, 2002

(65) Prior Publication Data

US 2003/0153930 A1    Aug. 14, 2003

(30) Foreign Application Priority Data

Dec. 26, 2000   (EP) ............................................. 00204750

(51) Int. Cl.
A61B 17/04   (2006.01)

(52) U.S. Cl. .................................... 606/151; 157/158
(58) Field of Classification Search .................. 606/151, 606/158
See application file for complete search history.

(56) References Cited

U.S. PATENT DOCUMENTS

| | | | | | |
|---|---|---|---|---|---|
| 2,143,910 A | * | 1/1939 | Didusch | ...................... | 606/151 |
| 3,665,926 A | * | 5/1972 | Flores | ........................ | 606/139 |
| 4,271,828 A | * | 6/1981 | Angelchik | .................. | 600/37 |
| 4,821,719 A | * | 4/1989 | Fogarty | ...................... | 606/158 |
| 5,171,253 A | * | 12/1992 | Klieman | ..................... | 606/158 |
| 5,258,005 A | * | 11/1993 | Christian | ..................... | 606/205 |
| 5,336,231 A | * | 8/1994 | Adair | .......................... | 606/148 |
| 5,337,736 A | * | 8/1994 | Reddy | ......................... | 600/217 |
| 5,536,251 A | * | 7/1996 | Evard et al. | ............. | 604/93.01 |
| 5,618,307 A | | 4/1997 | Donlon et al. | | |
| 5,674,220 A | * | 10/1997 | Fox et al. | ..................... | 606/51 |

* cited by examiner

Primary Examiner—Gary Jackson
(74) Attorney, Agent, or Firm—Townsend and Townsend and Crew LLP

(57) ABSTRACT

A surgical clamping device for hollow anatomical structures such as, essentially, blood vessels, but also for tracheas, intestines, etc. This device comprises a flexible guide and two jaws, each jaw being formed of an elongate member pierced with a longitudinal canal and having a distal end and a proximal end. These jaws can be slipped over the guide with their proximal end facing toward each of the ends of the guide. A mandrel is slipped over the two ends of the guide and brings the axes of the two jaws closer together, thus pinching the anatomical structure. This surgical clamping device applies more particularly to the clamping of the aorta.

14 Claims, 5 Drawing Sheets

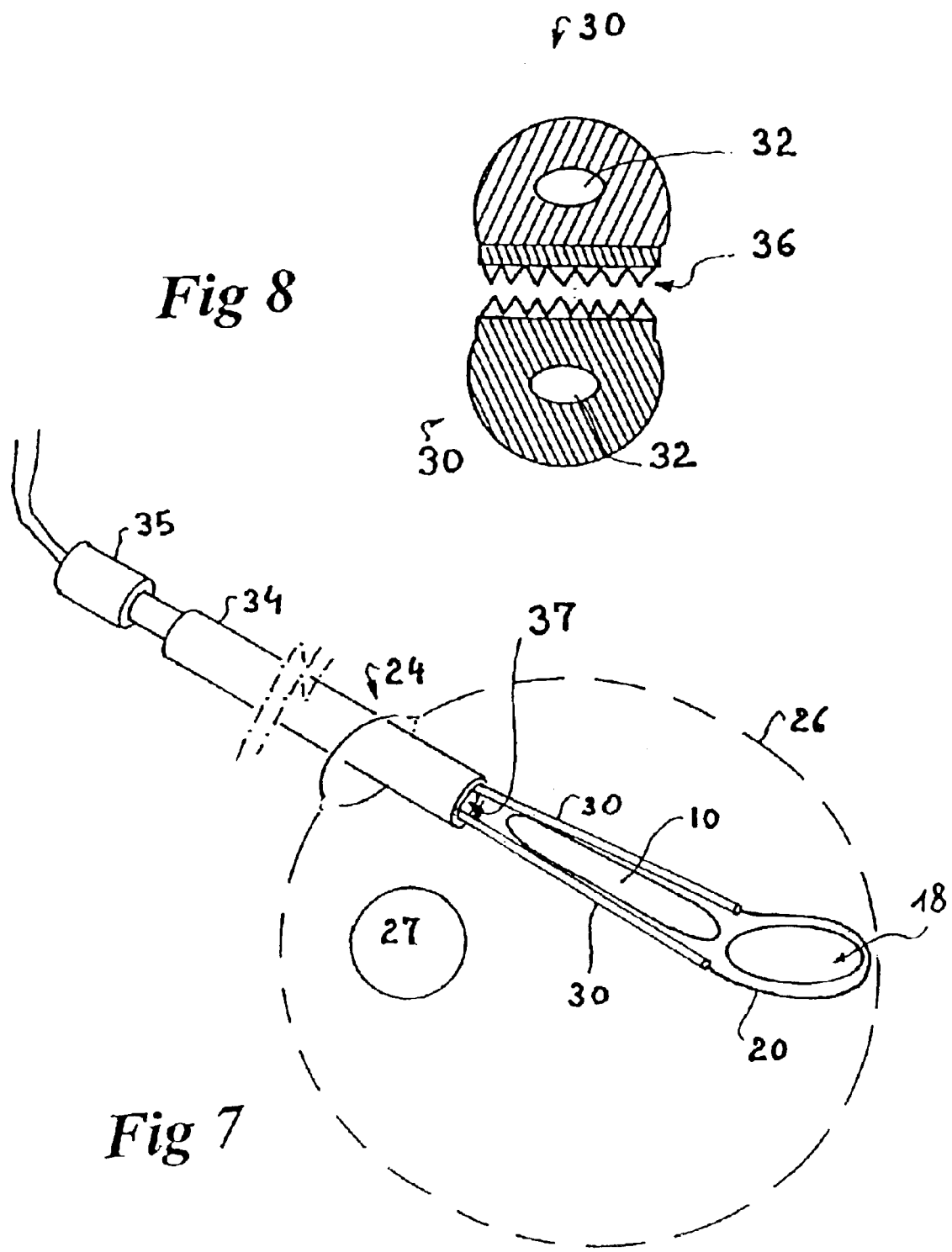

CLAMPING DEVICE FOR ANATOMICAL STRUCTURE

The invention relates to clamping devices for hollow tubular anatomical structures such as, essentially blood vessels, but also for tracheas, intestines, etc.

TECHNICAL BACKGROUND OF THE INVENTION

Heart surgery usually requires stopping the heart so as to obtain a stationary and exsanguinous operating site allowing a precise and delicate surgical operation. This entails: 1) resorting to extra-corporeal circulation (ECC) so as to perfuse the systemic organs (brain, liver, kidneys, etc.) with oxygenated blood for the period during which the heart is stopped.

2) clamping the aorta, which consists in blocking the vessel using external forceps which are applied between the arterial cannula allowing extra-corporeal circulation and the orifice of the coronary arteries. This operation isolates the coronary circulation from the blood flow supplied by the ECC and therefore allows the heart to be stopped.

3) Cardioplegy: injection of a solution into the network of coronary arteries to protect the heart itself during the period of arrest.

Hooking up the extra-corporeal circulation (ECC), clamping and cardioplegy conventionally entail cutting and parting the sternum (sternotomy). Sternotomy is a destructive surgical approach that carries significant post-operative risks to the patient.

Furthermore, clamping the aorta is an operation which is considered to be delicate and high risk because, in particular, of the proximity of the pulmonary artery, the texture of which is known to be extremely fragile.

What is more, clipping the artery using a conventional clamp is a source of embolism of atheromatous material which, in most cases, lines the internal wall of the vessel.

For many years, heart surgery has been developing alternative techniques aimed at being less aggressive toward the patient. Doing away with the sternotomy is one of these approaches. In this case, the operation is carried out using mini-incisions allowing endoscopic instruments to be introduced.

In this type of operation, when the heart needs to be stopped, an inflatable balloon is introduced into the aorta, where it leaves the heart, under echographic or fluoroscopic guidance, to clamp the aorta from inside the vessel.

This system has numerous disadvantages including, in particular, its cost, which limits its use to a number of marginal cases. Furthermore, this technique also dislodges particles carried along by the blood flow.

There is no alternative at the present time which is able to interrupt the circulation of the blood in the aorta without opening up the thorax.

BRIEF DESCRIPTION OF THE INVENTION

An alternative solution allowing a great amount of patients to undergo minimally invasive heart surgery in complete safety has therefore been sought.

The subject of the invention is a surgical clamp which comprises
a flexible guide;
two jaws each formed of an elongate member pierced with a longitudinal canal and having a distal end and a proximal end. Said jaws are so designed that they can be slipped over the guide with their proximal end facing toward each of the ends of the guide;
a mandrel that can be slipped over the two ends of the guide and over the jaws and which is able to bring the axes of the two jaws closer together and thus perform pinching.

The jaws are preferably closed by a control rod slipped over the two ends of the guide upstream of the mandrel.

Advantageously, an intermediate sheath is fitted using the guide. This flexible sheath may be positioned in the thorax facing a vascular structure encircled by the guide.

The jaw elements preferably have a malleable section at their proximal end.

According to one advantageous embodiment, the mandrel comprises a single longitudinal canal, the distal end of this cavity being shaped in such a way as to cause the axes of the two jaws to be moved closer together by relative displacement.

According to another advantageous embodiment, the mandrel comprises two longitudinal canals, each of the two jaws being slipped into one of the two canals.

The jaws are preferably provided with flexible jaw elements near their distal end.

According to an advantageous embodiment, the jaws are clamped together using a securing device with a single articulation or multiple articulations.

The jaws are preferably closed by a control slipped over the two ends of the guide upstream of the mandrel.

The proximal part of the jaws is advantageously equipped with ribbing collaborating with a mechanism supported by the mandrel.

The mechanism supported by the mandrel preferably comprises at least one pawl equipped with a nose and with a resilient part bringing said nose into contact with the ribbing of the jaws.

Another subject of the invention is a method of clamping a blood vessel comprising the following operations:
making a porthole in a warm-blooded organism,
introducing a flexible guide into said porthole,
causing the distal end of this guide to reemerge from the porthole,
slipping over each of the ends of the flexible guide an elongate member equipped with a longitudinal canal, with a distal part and with a proximal part,
bringing the distal ends of these two elongate members one onto each side of a blood vessel) that is to be clamped,
slipping a hollow mandrel over the proximal ends of these elongate members,
causing the hollow mandrel to move forward toward the distal end of the elongate members, thus causing the elongate members to move closer together and to pinch the blood vessel.

In this clamping method, the blood vessel may be a coronary artery, said method further comprising the following operations:
making a porthole in a thorax,
making an incision in the pericardium,
and introducing the flexible guide into the transverse sinus (Theile's).

The advantage of the clamp of the invention is that effective and powerful clamping is obtained through a minimal incision, of the order of one centimeter long, thus making the operation extremely minimally invasive.

The device of the invention applies particularly advantageously to the clamping of the aorta by using the anatomical space of Theile's transverse sinus as a natural guide.

Another advantage is that the risk of damaging an adjacent organ is reduced to a minimum. Particularly in the case of cardiac operations, the risk of tearing the pulmonary artery becomes practically negligible, because it is no longer necessary to make the dissection in the virtual plane between the two vessels.

The clamp of the invention can be used with equal ease for intra-thoracic and extra-thoracic vascular structures and for other anatomical structures including, in particular, the intestines. It may also be used as forceps for manipulating bones.

BRIEF DESCRIPTION OF THE DRAWINGS

Other particulars and advantages of the invention will become apparent from the description hereinafter of some particular embodiments of the invention, reference being made to the appended drawings in which:

FIGS. 3 to 7 are schematic views of the principle of clamping of the device of the invention.

FIG. 8 is a view in section of a pair of jaw elements of the clamp of the invention.

DETAILED DESCRIPTION OF THE INVENTION

Figure 1:
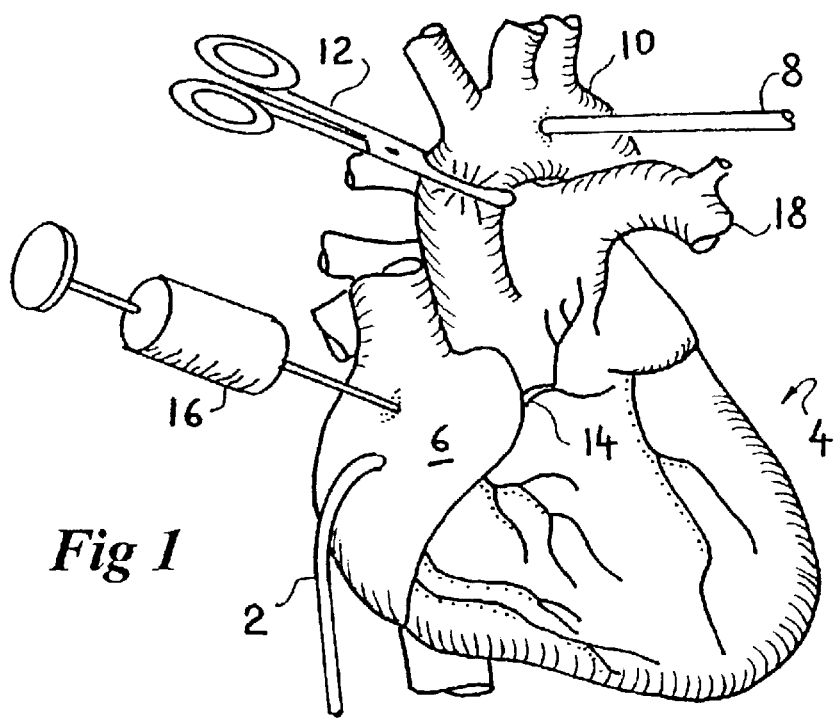
FIG. 1 is a perspective schematic view of the clamping of a human heart in the case of an operation with a sternotomy.

FIG. 1 shows the various operations in preparation for a conventional heart operation, so as to obtain an exsanguinous and stationary operation field.

Venous blood (low in oxygen) is diverted down a cannula 2 as it enters the heart 4 via the right atrium 6 toward a heart-lung machine (not depicted) which namely reoxygenates it and rids it of its $CO_2$. The artificially oxygenated blood is then returned by a second cannula 8 at the aorta 10 into the patient's arterial circuit, thus short-circuiting the heart 4 and the pulmonary circulation so as to allow the intra-cardiac or extracardiac operation to be performed.

The heart 4 can therefore be stopped in order to obtain an exsanguinous and stationary operating field.

The heart is conventionally stopped using two joint operations:
  clamping the aorta;
  injecting a cardioplegy solution into the coronary circulation.

Clamping the aorta 10 consists in blocking the vessel using external forceps 12 which are applied between the arterial cannula 8 of the extra-corporeal circulation and the orifice of the coronary arteries 14. This operation isolates the coronary circulation from the blood flow generated by the ECC.

A cardioplegy solution can then be injected by an injection member 16 into the coronary circulation to "paralyze" the heart 4 with a view to allowing the surgeon to operate more precisely then he could on moving anatomical structures.

Figure 2:
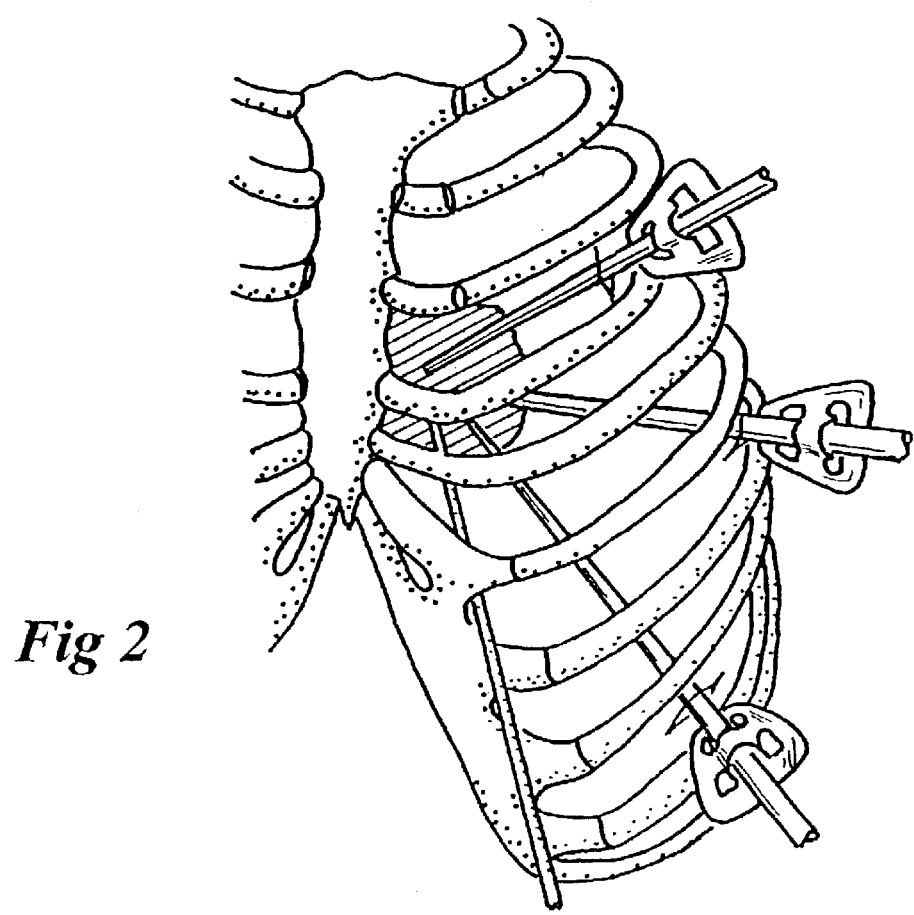
FIG. 2 is a view with cutaway of a heart operation with a mini-intercostal incision.

FIG. 2 shows another known approach, in which a heart operation is conducted via one or more incisions of the order of one centimeter long, allowing endoscopic instruments to be introduced.

The problem that arises in this case is that of reliably interrupting the circulation of the blood through the aorta, while at the same time avoiding the disadvantages inherent to introducing a balloon.

As was stated earlier, it is impossible to resort to conventional forceps in which the size of the jaws and their travel are out of proportion with the size of the intercostal incisions made.

The major advantage of the system according to the invention is that it allows the clamping to be performed without opening up the thorax but, what is more, with a lower risk of trauma to the pulmonary artery and of embolism.

The clamping device of the invention and its various components will be described with reference to the succession of FIGS. 3 to 7.

Figure 3:
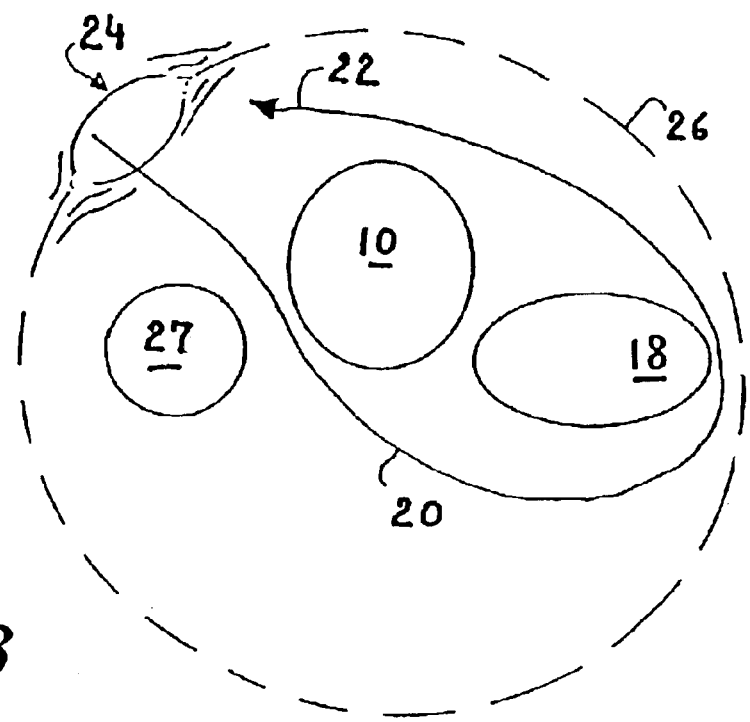
Figure 4:
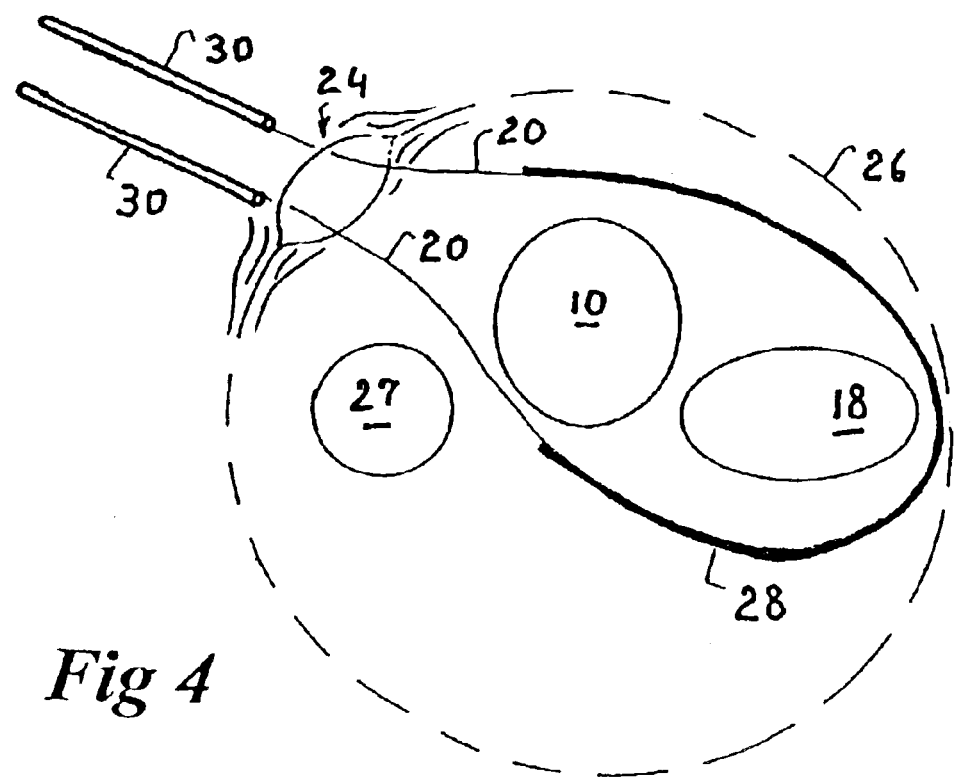
Figure 5:
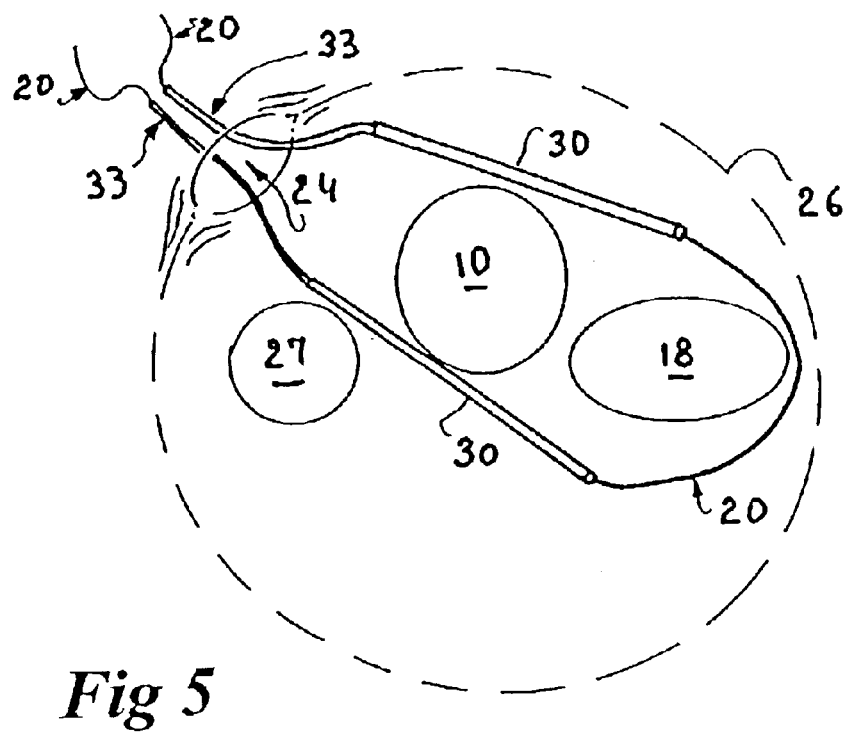
Figure 6:
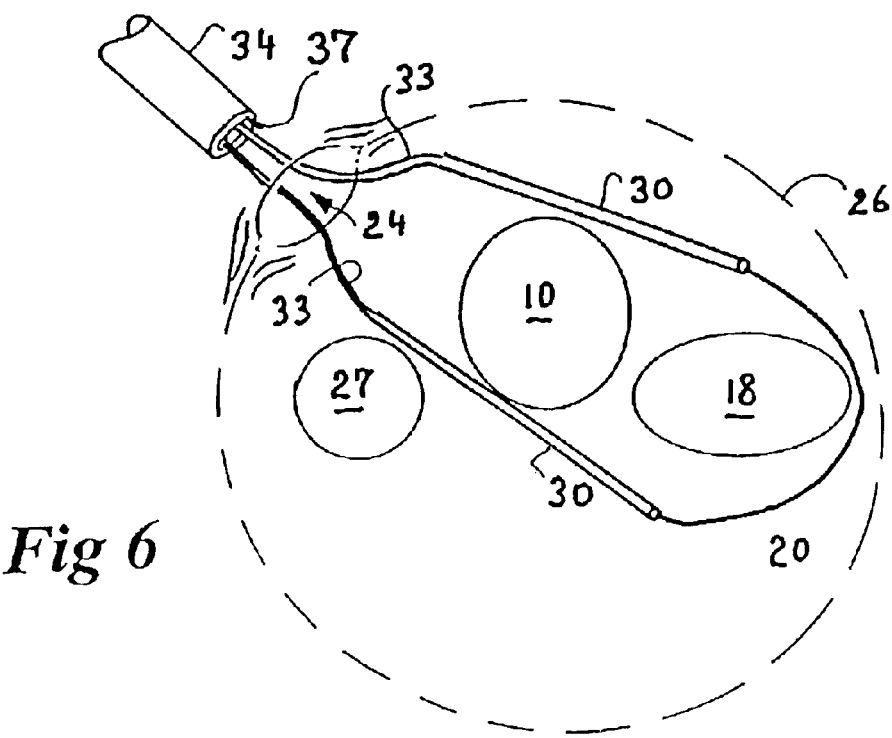

A flexible guide 20, possibly equipped with a steerable end 22, is introduced into the thorax from the left or the right through a porthole, then through an incision 24 in the pericardium into Theile's transverse sinus, a natural virtual anatomical space 26 covered with pericardiac serosa. All that is required is for the flexible guide 20 to be pushed so that it reappears, encircling the vessels that are to be clamped. In this particular instance, these are the large vessels at the base of the heart, that is to say the aorta 10 and the pulmonary artery 18. The guide makes it possible to avoid other organs (such as, in this instance, the superior vena cava 27). The end 22 of this guide 20 is then recaptured by a counter-incision if necessary, and reemerges through the same porthole (FIG. 3).

Depending on the mechanical properties of the guide and on the nature of the vessels that are to be clamped, an intermediate sheath 28 (FIG. 4) is slipped over the flexible guide 20. In another technique, this intermediate guide 28 is attached to one of the ends of the guide and hauled into place.

The operator next (FIG. 4) slips over each of the ends of the guide 20 (or of the intermediate sheath 28), a jaw 30 formed of an elongate member pierced with a longitudinal canal 32 (visible in FIG. 8), these jaws 30 are moved in such a way that their distal ends position themselves one on each side of the vessel to be clamped (in this instance the aorta 10). The jaws 30 depicted in FIGS. 5 and 6 differ from the jaws 30 of FIG. 4 in that they each comprise a malleable part 33 at their proximal end.

With the jaws 30 in place, the operator slips over the two ends of the flexible guide 20 a hollow mandrel 34 (FIG. 6) and causes this mandrel 34 to move back toward the proximal end of the jaws 30 (FIG. 7). The jaws 30 then each align with the axis of the mandrel 34 and move closer together, causing delicate and gradual pinching of the aorta 10.

The device that brings about pinching may be arranged in different ways:

In its simplest design, the proximal part of the jaws comprises a conical surface which collaborates with the mouth of the longitudinal canal 37 of the mandrel 34, causing the jaws to align. This canal 37 may be a single or double canal. The jaws may also be equipped with ribbing collaborating with a screw thread formed at the interior surface of the mandrel 34.

In another arrangement (FIG. 7), a part 35 which can move with respect to the mandrel 34 is mounted on the two proximal ends of the jaws 34. By relative movement of this part 35 with the mandrel 34, particularly by way of a threaded part, the jaws 30 can be clamped or slackened.

FIG. 8 shows, in cross section, the distal part of the jaws 30. In this embodiment, these are provided with flexible jaw elements 36 so as to spread the pressure over the organ which has been grasped. It is possible on this section view to make out the longitudinal canal 32 allowing the guide 20 to be passed.

Figure 9:
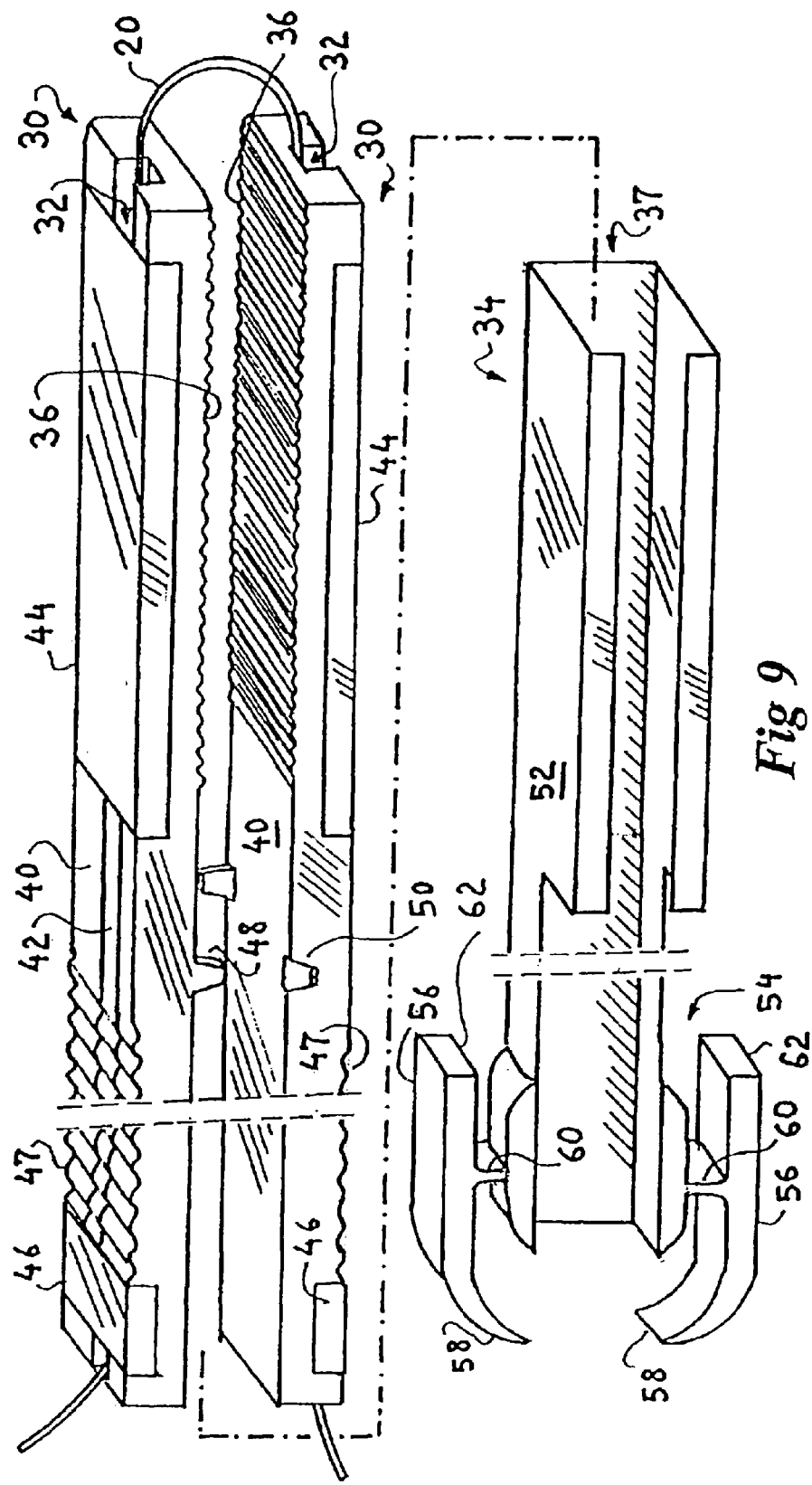
FIG. 9 is an exploded view of one form of embodiment of the clamp of the invention.

FIG. 9 shows, dismantled, one embodiment of the clamp of the invention. Each member forming a jaw 30 comprises a tongue 40 made of plastic. The faces of these tongues which face toward each other and are slightly toothed, form the jaw elements 36. The back of each tongue 40 comprises a longitudinal groove 42 intended to accommodate the flexible guide 20.

The distal part of the tongues 40 is gripped in a U-shaped metal section piece 44 which closes the longitudinal canal 32 and gives the jaws 30 the rigidity they need to exert the pinching action. A second U-shaped part 46 closes another segment of the longitudinal canal near the other end of each tongue 40. The back of the proximal part of the tongues is ribbed 47.

Each of the tongues 40 carries, at its central part, a stud 48 and a cavity 50 which are intended to engage in the corresponding parts 50, 48 of the other tongue 40 so as to prevent any relative movement of the jaws once their ends are inserted in the mandrel 34.

In this form of embodiment, the mandrel 34 is itself essentially formed of a metal part 52 bent over on itself. At the distal end, this metal part has a C-shaped section which allows the jaws 30 to be inserted into it and guided therein.

The proximal part of the mandrel 34 supports a mechanism that allows the relative position of the jaws 30 and of the mandrel 34 to be adjusted. This mechanism comprises a double pawl 56, 56. At rest, the nose 58 of each of the pawls 56 is engaged in the proximal ribbing 47 of the tongues 40 via a part that forms a spring 60. Pressure on the heel 62 of the pawls 56 releases the tongues 40, and thus allows the jaws 30 to slide freely with respect to the mandrel 34.

What is claimed is:

1. A surgical clamp which comprises
   a flexible guide having two ends;
   two jaws, each jaw being formed of an elongated member having an axis and pierced with a longitudinal canal and having a distal end and a proximal end, said jaws being designed so as to slip over the guide with their proximal end facing toward each of the ends of the guide;
   a mandrel configured to be slipped over the two ends of the guide and which is able to bring the axes of the two jaws closer together.

2. The surgical clamp as claimed in claim 1, further comprising an intermediate sheath configured to slip over the guide.

3. The surgical clamp as claimed in claim 1, wherein the jaws have a malleable section at their proximal end.

4. The surgical clamp as claimed in claim 1, wherein the mandrel comprises a single longitudinal canal, the distal end of this canal being shaped in such a way as to cause the axes of the two jaws to be moved closer together by relative displacement.

5. The surgical clamp as claimed in claim 1, wherein the mandrel comprises two longitudinal canals, each of the two jaws being slipped into one of the two canals.

6. The surgical clamp as claimed in claim 1, wherein the jaws are provided with flexible jaw elements near their distal end.

7. The surgical clamp as claimed in claim 1, wherein the jaws are clamped using a securing device with a single articulation or multiple articulations.

8. The surgical clamp as claimed in claim 1, wherein the jaws are closed by a control slipped over the two ends of the guide upstream of the mandrel.

9. The surgical clamp as claimed in claim 1, wherein the proximal part of the jaws is equipped with ribbing collaborating with a mechanism supported by the mandrel.

10. The surgical clamp as claimed in claim 9, wherein the proximal part of the jaws is equipped with ribbing collaborating with a mechanism supported by the mandrel.

11. The surgical clamp as claimed in claim 9, wherein the mechanism supported by the mandrel comprises at least one pawl equipped with a nose and with a resilient part bringing said nose into contact with the ribbing of the jaws.

12. The surgical clamp as claimed in claim 10, wherein the mechanism supported by the mandrel comprises at least one pawl equipped with a nose and with a resilient part bringing said nose into contact with the ribbing of the jaws.

13. A method of clamping a blood vessel comprising the following operations:
    making a porthole in a warm-blooded organism,
    introducing a flexible guide into said porthole,
    causing a distal end of this guide to reemerge from the porthole, encircling the structure to be clamped,
    slipping over each of the ends of the flexible guide an elongate member equipped with a longitudinal canal, with a distal part and with a proximal part,
    bringing the distal ends of these two elongate members one onto each side of a blood vessel that is to be clamped,
    slipping a hollow mandrel over the proximal ends of these elongate members,
    causing the hollow mandrel to move toward the distal end of the elongate members, thus causing the elongate members to move closer together and to pinch the blood vessel.

14. The method of clamping a blood vessel as claimed in claim 13 in which the blood vessel is a the aorta artery, said method further comprising the following operations:
    making a porthole in the thorax of said organism,
    making an incision in the pericardium of said organism,
    introducing the flexible guide into Theile's transverse sinus.

* * * * *